US005252829A

United States Patent [19]
Nygaard et al.

[11] Patent Number: 5,252,829
[45] Date of Patent: Oct. 12, 1993

[54] METHOD OF DETERMINING UREA IN MILK

[75] Inventors: Lars Nygaard, Græsted; Torben Lapp, Birkerød; Börkur Arnvidarson, Nivå, all of Denmark

[73] Assignee: A/S Foss Electric, Hillerod, Denmark

[21] Appl. No.: 885,642

[22] Filed: May 19, 1992

[30] Foreign Application Priority Data

Mar. 25, 1992 [DK] Denmark ........................ 397/92

[51] Int. Cl.$^5$ ...................... G01N 33/04; G01N 21/35
[52] U.S. Cl. ..................................... 250/339; 250/343
[58] Field of Search .............. 250/339, 340, 341, 343, 250/345

[56] References Cited

U.S. PATENT DOCUMENTS

| | | |
|---|---|---|
| 4,169,676 | 10/1979 | Kaiser . |
| 4,447,725 | 5/1984 | Biggs et al. ............... 250/340 X |
| 4,663,530 | 5/1987 | Shields ..................... 250/343 X |
| 4,855,601 | 8/1989 | Savoyet ..................... 250/339 |
| 5,017,785 | 5/1991 | Räsänen ..................... 250/345 |

FOREIGN PATENT DOCUMENTS

| | | |
|---|---|---|
| 0382908 | 8/1990 | European Pat. Off. . |
| 0404562 | 12/1990 | European Pat. Off. . |
| WO9206373 | 4/1992 | PCT Int'l Appl. . |
| 420914 | 8/1974 | U.S.S.R. ..................... 250/341 |

OTHER PUBLICATIONS

"Multivariate Calibration for Assays in Clinical Chemistry Using Attenuated Total Reflection Infrared Spectra of Human Blood Plasma", by G. Janatsch et al., Anal. Chem. 1989, 61, 2016-2023.
J. Clin. Chem. Clin. Biochem., vol. 26, 1988/No. 11, p. 749.
Clinical Chemistry, vol. 36, No. 2, 1990, pp. 401-402.
"The Composition of Milk: The Determination of Protein by the IR Method", Meijeritieteellinen Aikakauskirja XLI, No. 2, pp. 40-55, 1983.

Primary Examiner—Constantine Hannaher
Assistant Examiner—Edward J. Glick

[57] ABSTRACT

The concentration of urea in a concentration range of 0–0.1% in a milk sample containing at least 1% fat, at least 1% dissolved lactose, and at least 1% protein, is determined with an accuracy better than 0.007%, expressed as Standard Error of Prediction, by an infrared attenuation measuring technique, by determining, on the sample, the attenuation in the region of infrared radiation from 1000 cm$^{-1}$ (10.0 µm) to 4000 cm$^{-1}$ (2.50 µm), at least one determination being made in a waveband in the region from 1000 cm$^{-1}$ (10.0 µm) to 1800 cm$^{-1}$ (5.56 µm) in which urea absorbs, at least one other determination being made in a waveband in which fat absorbs, at least one further determination being made in a waveband where lactose absorbs, and at least one further determination being made in a waveband where protein absorbs; determining, on the basis of the thus determined attenuations and predetermined parameters established by multivariate calibration, the contribution from fat, lactose, and protein in the waveband where urea absorbs, and quantitatively assessing the concentration of urea in the sample on the basis of the absorption in the waveband where urea absorbs, and on the basis of the determined contribution from fat, lactose and protein in said waveband. The multivariate calibration may be performed by a Partial Least Squares algorithm, Principal Component Regression, Multiple Linear Regression, or Artificial Neural Network learning. Using the method according to the invention, compensation for the influence on the urea measurement may further be performed for one or several of the following components: citric acid, free fatty acids, antibiotics, phosphates, somatic cells, bacteria, preservatives and casein.

27 Claims, 5 Drawing Sheets

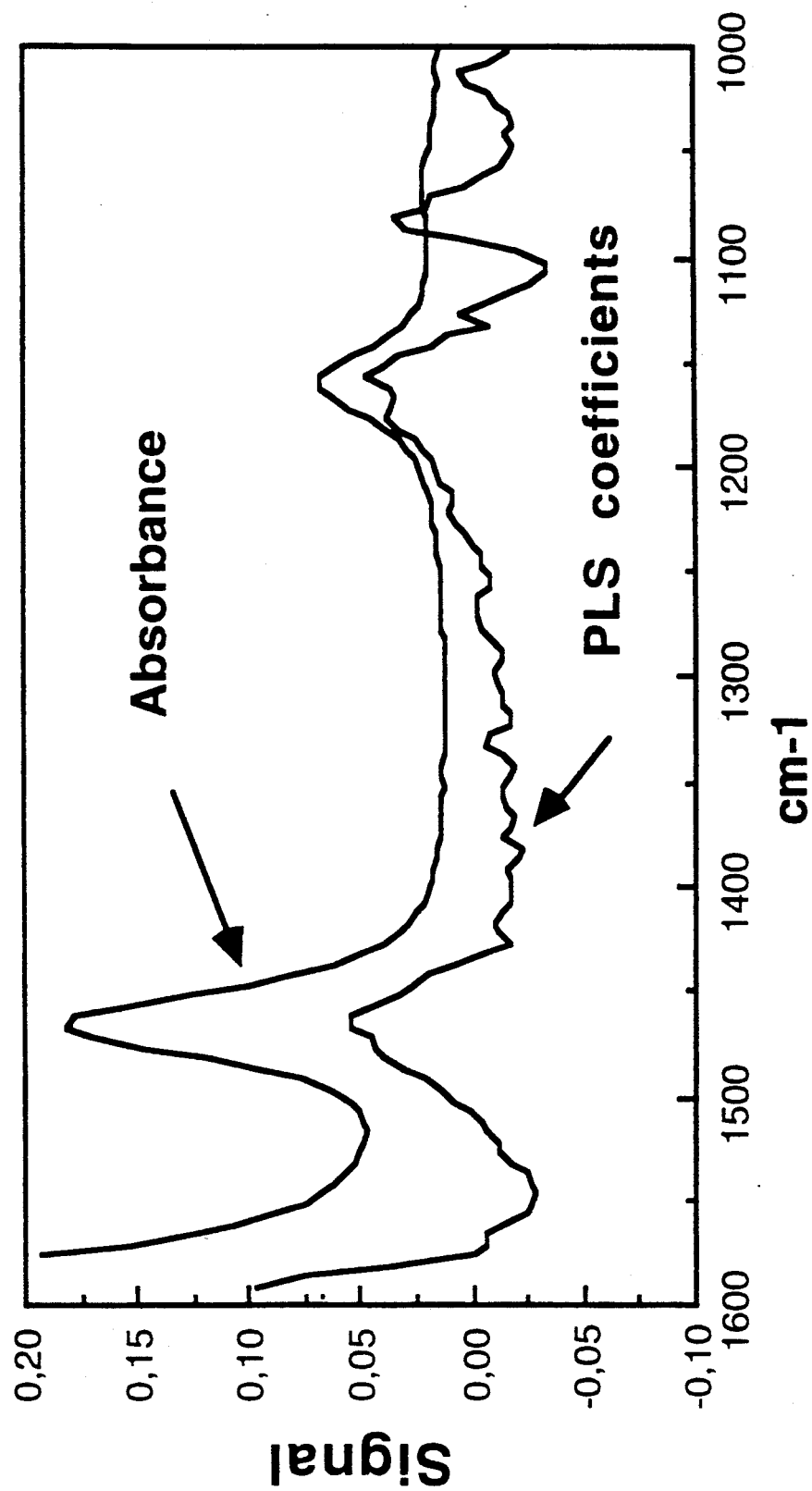

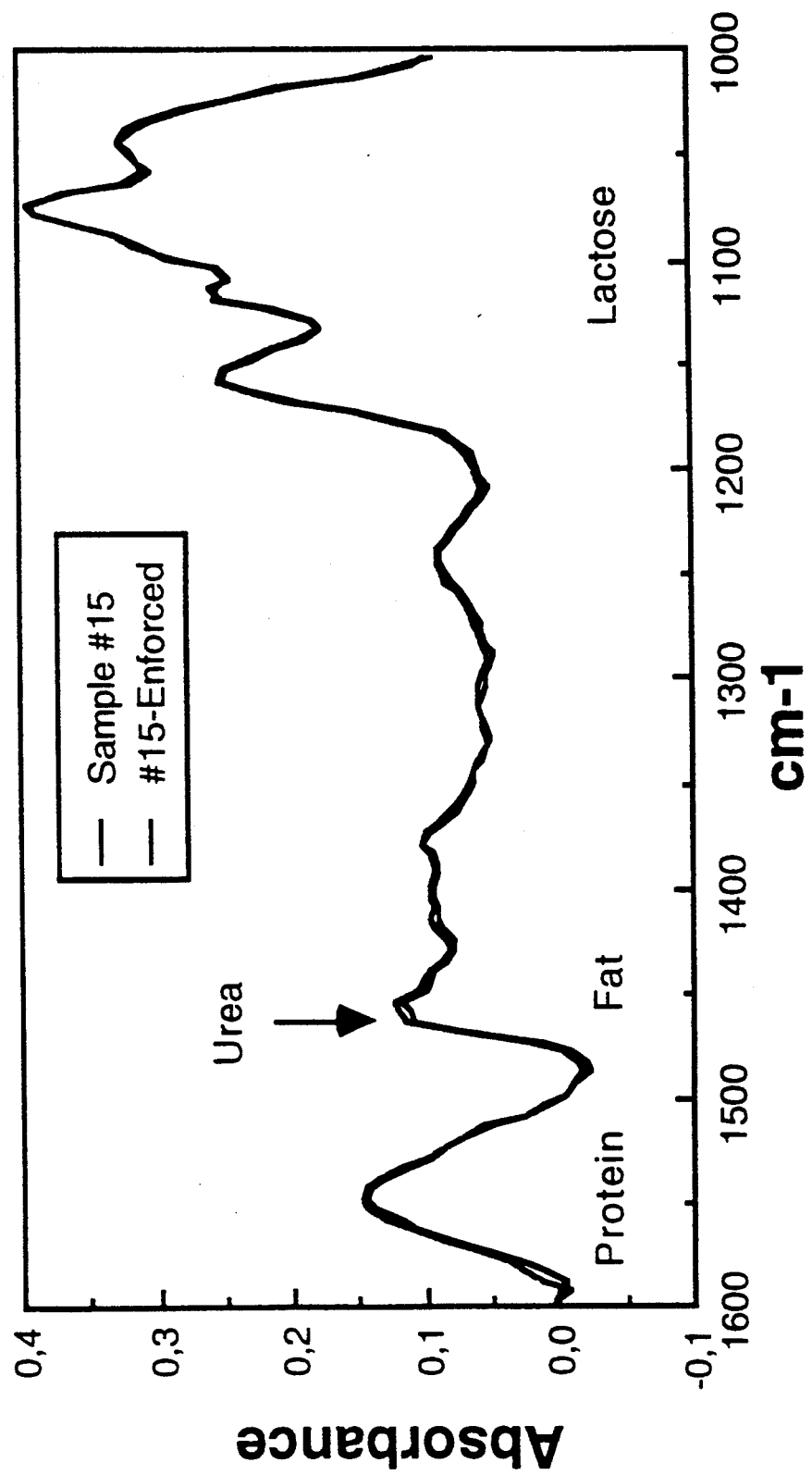

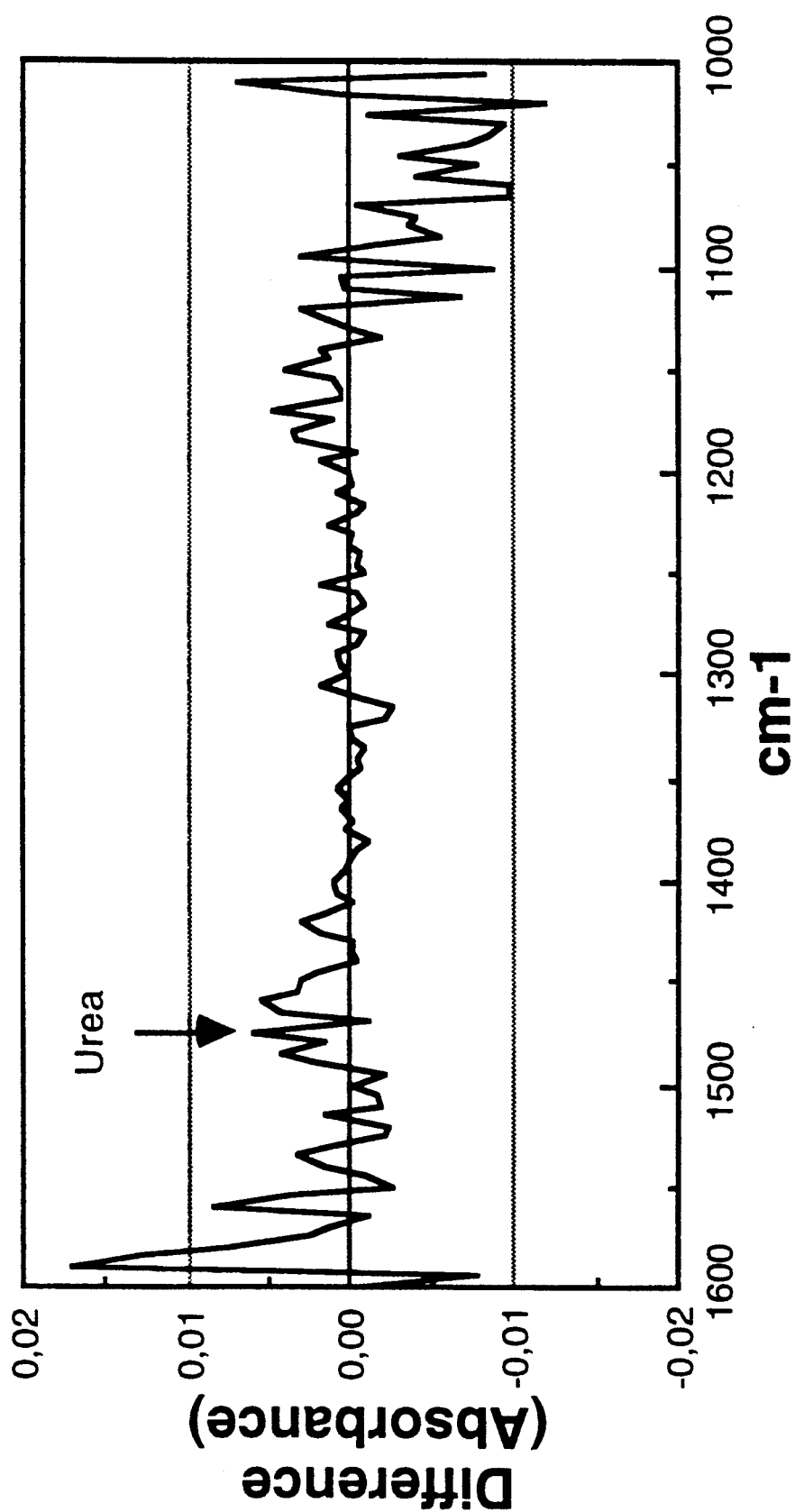

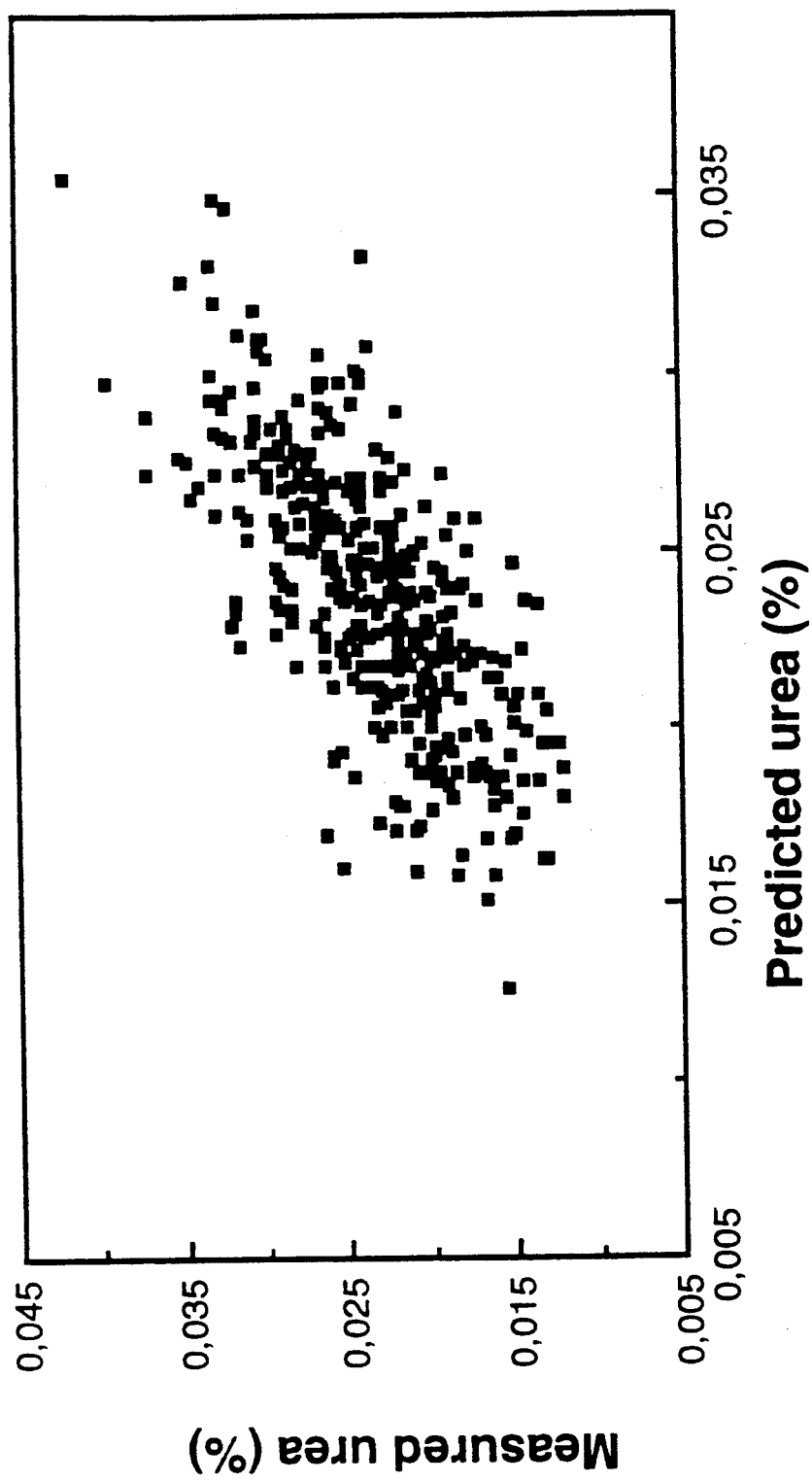

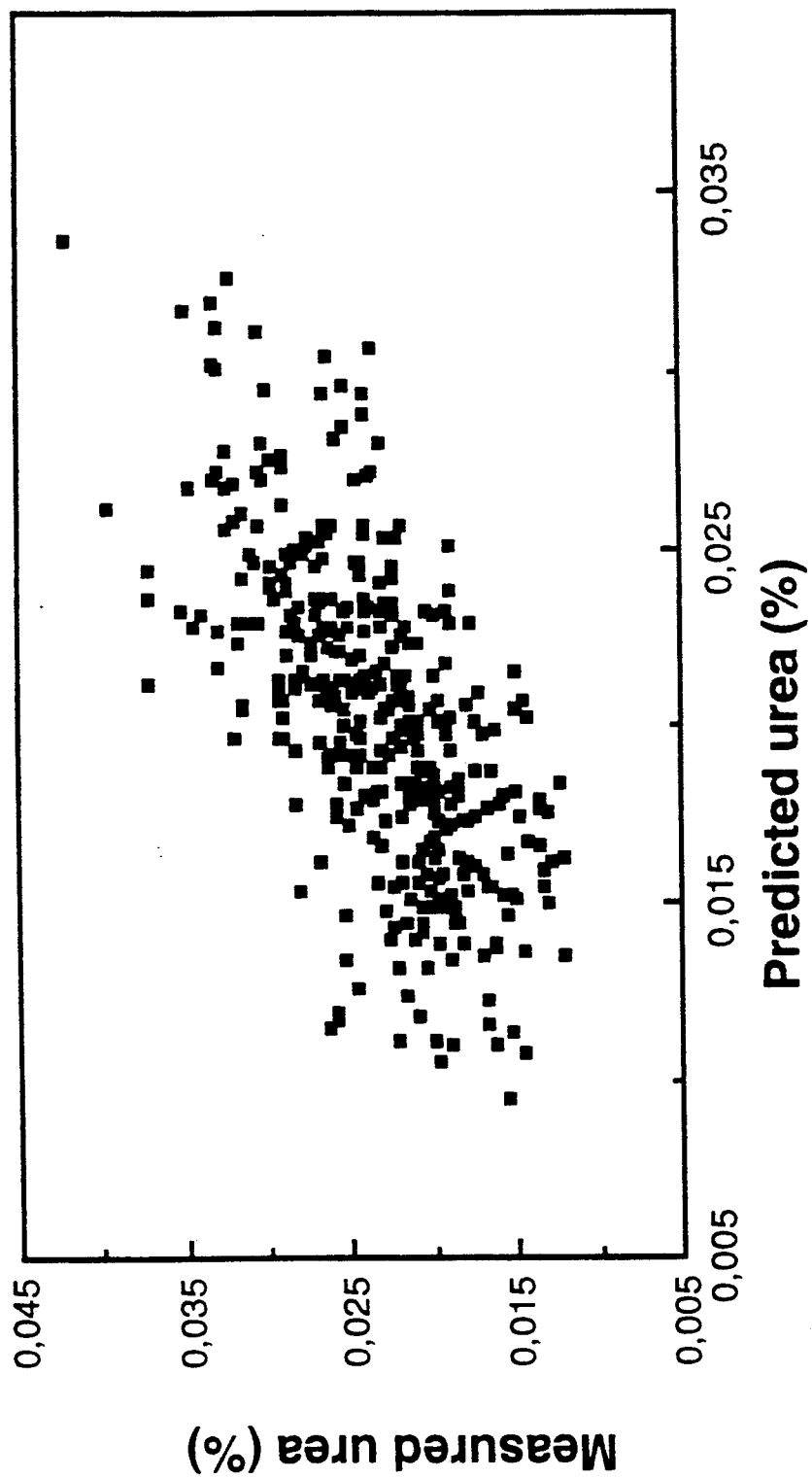

METHOD OF DETERMINING UREA IN MILK

FIELD OF THE INVENTION

The present invention relates to a method for determining the concentration of urea in a milk sample.

DESCRIPTION OF THE RELATED ART

Urea is present in milk in very small concentrations in the range of, normally, 0.01–0.06%. The concentration of urea in milk, in particular raw milk, combined with the concentration of protein, is an important factor in the regulation of feeding of the livestock. Therefore, it is of great importance to be able to determine the concentration of urea in milk on a regular basis. However, the methods available for this purpose until now, are predominantly based on a determination of ammonia formed in enzymatic breakdown of urea with urease, are time-consuming and require relatively expensive reagents, for which reason the determination is normally performed at relatively long intervals, such as 1–3 months, which, however, is unsatisfactory from the point of view of effective farm management.

Infrared light measurements offer the means of rapid and inexpensive measurement of the components of milk. However, due to the relatively small amounts of urea compared to the variations of the major components of milk, and the fact that the spectral features of these components coincide with the spectral features of urea, in other words, there is no specific absorption wavebands characteristic to only urea, the known methods for determining components of milk by infrared light measurement are not able to provide useful information about urea concentration.

The known methods for infrared determination of milk components are performed as follows:

Apart from measuring the attenuation of light in a waveband showing a characteristic absorption of a component to be determined, such as, e.g., fat, the absorption in a waveband in the near vicinity and substantially representing the background (the influence from other components) is measured and subtracted from the result of the first measurement, thereby obtaining correction for spectral phenomena caused by interfering components. However, due to the exceedingly low concentration of urea compared to the major components of milk (e.g. fat, which absorbs in the same wavebands as urea, is normally present in amounts which are about 100–500 times larger than the amounts of urea, and can vary by amounts themselves are, e.g. 50–200 times the absolute amount of urea present, and similar effects apply in a lesser degree to the other major components of milk), and also due to the high degree of spectral interferences from those components, the known method cannot be used.

In addition milk is a heterogeneous system, consisting of dissolved substances, fat globules, and protein micelles, all of which contribute to infrared light attenuation, thus making the measurement of the contribution ascribable to absorption even more complex.

According to the invention, it has now been found that it is possible to determine urea quantitatively and with a high degree of accuracy in a milk sample using an infrared measurement.

SUMMARY OF THE INVENTION

Thus, the invention relates to a method for determining the concentration of urea in a concentration range of 0–0.1% in a milk sample containing at least 1% fat, at least 1% dissolved lactose, and at least 1% protein, by an infrared attenuation measuring technique, said method comprising determining, on the sample, the attenuation in the region of infrared radiation from 1000 $cm^{-1}$ (10.0 $\mu m$) to 4000 $cm^{-1}$ (2.50 $\mu m$) at least one determination being made in a waveband in the region from 1000 $cm^{-1}$ (10.0 $\mu m$) to 1800 $cm^{-1}$ (5.56 $\mu m$) in, which urea absorbs, at least one other determination being made in a waveband in which fat absorbs, at least one further determination being made in a waveband where lactose absorbs, and at least one further determination being made in a waveband where protein absorbs; and calculating (predicting) the concentration of urea, an accuracy, expressed as Standard Error of Prediction (SEP, as defined herein), better than 0.007%, based on the absorption in the waveband where urea absorbs, the contribution from fat, lactose, and protein being compensated for on the basis of multivariate calibration by combining the results from the determinations made in the wavebands where these components absorb.

Using the method of the invention, it is possible to determine the urea content with a degree of accuracy which is several orders of magnitude better than the variation of the interfering components. Due to the above-mentioned highly complex character of milk as an attenuating system, it could not be anticipated that it would be possible by any technique to arrive at such accuracies, better than a Standard Error of Prediction (as defined below) of 0.007%, and typically better than 0.005% or even 0.004%.

In order to give an impression of the completely surprising accuracy achieved according to the present invention, it can be mentioned that the obtainable accuracy in the determination of fat, protein and lactose in milk is of the order of 0.01–0.02% absolute. This can be compared with the normal level of urea, which is about 0.025%. In other words, the total content of urea is about the same as the obtainable accuracy in the determination of the other components. In spite of this, the method according to the invention is capable of determining the extremely minor component urea with a standard error which is of the order of 0.003–0.004% absolute.

Thus, the invention provides an easy and economic method of determining urea in milk, so that it becomes realistic to perform frequent analysis on herd animals to improve farm management.

The multivariate calibration parameters used are preferably parameters which have been obtained using milk samples containing known concentrations of urea, or milk samples to which known concentrations of urea have been added.

The multivariate calibration is preferably performed by selecting the calibration samples in such a manner that the correlation between the components in the samples and other physical conditions of the sample (e.g. homogenization and temperature) is as low as possible; thus, e.g., it should be avoided that samples having a high content of urea at the same time predominantly have a high degree of homogenization, etc. This suitable selection of calibration samples is obtained, e.g., by having a large amount of calibration samples and selecting the ones to be used so that the set shows low correlation, or, as indicated above, by addition of a component, or other modification of a sample.

The term "milk sample" designates samples of milk and related products, such as raw milk, whole milk, skim milk, cream, redissolved and/or resuspended powdered milk. This sample may or may not be homogenized. In accordance with a preferred embodiment of the invention, the sample is a sample of raw milk.

While normal raw milk samples normally contain approx. 3.7% fat, 3.4% protein, 4.8% lactose, and 0.025% urea, the invention is contemplated to be most useful also in cases where the sample has a more unusual composition with a very low content of one or more of the components.

In the present context, the term "infrared attenuation technique" is intended to designate a measuring technique where light in the infrared range is transmitted to a sample, and the attenuation of the infrared light (which may be due to light scattering or energy absorption) caused by the sample is measured.

The infrared measuring technique may be a transmission technique which comprises transmitting the infrared light through a container which holds the sample, the container being made from a material transmitting the infrared light. When splitting the transmitted light into a suitable number of suitably selected wavebands and measuring the amount of light absorbed in each of the wavebands, it is possible to determine the concentration of one or more components in the sample.

An alternative way of introducing the infrared light in the sample is using an ATR-cell where the absorption of the light is facilitated by launching the light onto a boundary between the sample and a material which has a higher index of refraction than milk, e.g. ZnSe or Ge. Due to the nature of light the electromagnetic field will extend a few $\mu m$ across the boundary whereby it will experience the influence of the sample.

In an article: "Multivariate Calibration for Assays in Clinical Chemistry using ATR-IR spectra of Human blood plasma", Analytical Chemistry, 1989, 61, pp 2016-2023 by Günter Janatsch et. al., FTIR-ATR is used for measuring the concentration of urea, uric acid, cholesterol, triglycerides, and glucose in human blood plasma.

Blood plasma is a liquid containing a.o. fat (triglycerides, cholesterol), protein and carbohydrate (glucose). Typical values for the concentration of the components in blood plasma, and wavebands from which these concentrations may be determined are compared to typical concentrations of the components in raw milk in table 1.

TABLE 1

| compound | range (cm$^{-1}$) | $\mu m$ | concentration (%) Blood plasma | concentration (%) Milk |
|---|---|---|---|---|
| protein | 1700-1350 | 5.88-7.41 | 6.7 | 3.4 |
| glucose/lactose | 1180-950 | 8.47-10.0 | 0.1 | 4.8 |
| fat | 1500-1400 | 6.67-7.14 | 0.3 | 3.7 |
| | 1430-1150 | 6.94-8.70 | | |
| | 1275-1000 | 7.84-10.0 | | |
| urea | 1700-1400 | 5.88-7.14 | 0.03 | 0.025 |
| | 1200-1000 | 8.33-10.0 | | |
| Variation in urea | | | 0.005-0.13 | 0.01-0.06 |

From table 1 it is obvious that the two systems have quite different compositions. Raw milk usually contains more than an order of magnitude more fat than blood plasma. The fat in blood is mostly dissolved cholesterol, whereas, in milk, it is mostly in the form of suspended milk fat globules.

In milk, 80% of the protein is casein present in micelles having a diameter of 0.01-0.3 $\mu m$, only 20% being dissolved. In blood, all protein is dissolved.

There is more than a order of magnitude more carbohydrate in milk than in blood, the carbohydrate in blood is mostly glucose whereas in milk it is lactose.

BRIEF DESCRIPTION OF THE DRAWINGS

FIG. 1 illustrates the close resemblance of the regression coefficients found by a calibration to the spectral characteristics of urea dissolved in water.

FIG. 2 shows the spectra of a milk sample and of the sample enforced with urea.

FIG. 3 shows the difference-spectrum of the spectra of FIG. 2.

FIGS. 4 and 5 illustrates the correspondence between the measured urea values versus the values predicted on the basis of a calibration using 380 and 16 samples, respectively.

DETAILED DESCRIPTION OF THE PREFERRED EMBODIMENT

In the method of the present invention, measurements are made in one or more wavebands in the region of infrared radiation from 1000 cm$^{-1}$ (10.0 $\mu m$) to 4000 cm$^{-1}$ (2.50 $\mu m$). Of these wavebands at least one of which is in the region from 1000 cm$^{-1}$ (10.0 $\mu m$) to 1800 cm$^{-1}$ (5.56 $\mu m$) in which urea absorbs. In preferred embodiments the waveband in which urea absorbs is chosen from the group consisting of 1100 cm$^{-1}$ (9.09 $\mu m$) to 1800 cm$^{-1}$ (5.56 $\mu m$) 1400 cm$^{-1}$ (7.14 $\mu m$) to 1500 cm$^{-1}$ (6.67 $\mu m$), 1500 cm$^{-1}$ (6.67 $\mu$) to 1800 cm$^{-1}$ (5.56 $\mu m$), and 1100 cm$^{-1}$ (9.09 $\mu m$) to 1200 cm$^{-1}$ (8.33 $\mu m$). These wavebands are preferably selected so that the components in the sample have different and varying influence ratios (absorption ratios) in different wavebands.

By suitable selection of the wavebands determination of the concentration of urea may be performed using a minimum number of wavebands.

For defining the wavebands in which the absorption is to be measured, a number of waveband-selective elements may be used: optical filters, gratings, prisms, acousto optic modulators a.o.

In the present specification and claims, the term "waveband" designates a wavelength region the width and center value of which may be chosen within wide ranges by proper selection of the actual waveband selecting element used. Thus, e.g., optical filters normally define wavebands which may have a width of the order of about 10-40 cm$^{-1}$, but the wavebands in which measurement is made according to the present invention may, in principle, be much broader, or much narrower.

When using optical filters to define the individual wavebands, a number of filters may be successively placed in the path of the light beam between the light source and the detector. An alternative embodiment comprises splitting up the beam in a number of beams each passing one or more stationary or movable optical filters.

Using a grating, a number of wavebands may be selected by combining a movable grating with one or more stationary or movable detectors, or combining a stationary grating with one or more movable and/or stationary detectors.

When an FTIR technique is used, a spectrum of the transmission of the sample is produced from Fourier transformation of an interferogram produced by an interferometer. From the transmission spectrum the absorption in a waveband can be calculated. Irrespective of which particular infrared transmission attenuation technique is used, the sample container is preferably a cuvette made from $CaF_2$ and having a light path not longer than 200 μm, preferably not longer than 50 μm. To reduce the size of the fat globules, the samples may be homogenized so that the mean diameter of the fat globules in the sample is at the most 3 μm, preferably at the most 2 μm.

The multivariate calibration may be accomplished using a number of methods such as: Partial Least Squares algorithm, Principal Component Regression, Multiple Linear Regression or Artificial Neural Network learning.

In a preferred embodiment the methods Partial Least Squares algorithm and Principal Component Regression are used to reduce the waveband information to the more essential information whereby they avoid overfitting the prediction; overfitting may be a drawback of other methods.

The Standard Error of Prediction (SEP) is defined as the standard deviation of the difference between the result of the chemical reference method comprising enzymatic decomposition of urea to ammonium and carbonate, followed by spectrophotometric determination of ammonium as an indirect measure of urea, and the predicted value according to the invention.

In a preferred embodiment, the method according to the invention is adapted so that it also predicts the concentration of fat, protein, and lactose in the milk sample. For this purpose, the multivariate calibration is performed on the basis of milk samples containing known concentrations of fat, protein, lactose, and urea, and/or on milk samples to which known concentrations of urea, fat, lactose, and/or protein have been added. Additionally, the physical conditions (temperature, degree of homogenization) of the milk samples used to perform the multivariate calibration can be modified.

The method may be expanded so that the compensation for the influence on the urea measurement is further performed for one or several of the following components: citric acid, free fatty acids, antibiotics, phosphates, somatic cells, bacteria, preservatives and casein, by performing, for each component, determination of infrared attenuation in a waveband in which the component absorbs, the compensation being performed on the basis of multivariate calibration by combining the results, for all components for which compensation is to be made, from the determinations made in the wavebands where the components absorb.

The number of milk samples used for calibration is preferably as large as practically feasible. Normally, the number is at least 4, but it is preferred to use a higher number, and while any higher number is in principle of interest, such as from 5, 6, or 7 through 10, 20, 30, etc. up to, in principle 40, 50 or even more, practical considerations will also apply, and thus, reasonable preferences could be expressed as at least 8, more preferably at least 12 samples, still more preferably at least 15 samples, and still more preferably at least 16, 17, or 18 or maybe even up to 25 samples where calibration is performed with respect to urea, fat, lactose, protein, and citric acid, all of this provided that the samples are reasonably selected so that they show a useful variation of the contents of the various components, such as discussed above, the importance of the non-correlated variation of the samples increasing with decreasing sample number.

EXAMPLE 1

Measurement of Urea in an Infrared Attenuation Measuring System Using Milk Samples, Measured By Fourier Transform IR Spectrophotometer The sample material was prepared from a starting sample collection consisting of 37 raw milk samples.

Portions of each of the 37 samples were analyzed by reference methods for the determination of fat, protein, lactose, and urea, the reference methods being Röse-Gottlieb, Kjeldahl, Luff-Schoorl, and Flow Injection Analysis, using a method comprising enzymatic decomposition of urea to ammonium and carbonate, followed by spectrophotometric determination of ammonium as an indirect measure of urea, respectively. The composition of the samples is shown in the following table.

|    | Fat   | Protein | Lactose | Urea   | Enforced urea |
|----|-------|---------|---------|--------|---------------|
| 1  | 3.865 | 2.940   | 4.480   | 0.0162 |               |
| 2  | 3.860 | 3.615   | 4.310   | 0.0354 |               |
| 3  | 3.665 | 2.900   | 4.520   | 0.0288 |               |
| 4  | 4.640 | 3.585   | 4.305   | 0.0228 | 0.0381        |
| 5  | 5.740 | 4.455   | 4.395   | 0.0198 |               |
| 6  | 4.100 | 3.305   | 4.590   | 0.0246 |               |
| 7  | 3.280 | 3.110   | 4.505   | 0.0246 |               |
| 8  | 3.770 | 3.300   | 4.620   | 0.0216 | 0.0389        |
| 9  | 5.500 | 3.555   | 4.730   | 0.0228 |               |
| 10 | 3.840 | 3.920   | 4.020   | 0.0216 |               |
| 11 | 4.615 | 3.575   | 4.390   | 0.0252 |               |
| 12 | 4.085 | 3.220   | 4.605   | 0.0204 |               |
| 13 | 4.635 | 3.265   | 4.455   | 0.0192 |               |
| 14 | 5.835 | 3.490   | 4.505   | 0.0234 |               |
| 15 | 5.180 | 3.495   | 4.525   | 0.0168 | 0.0552        |
| 16 | 5.395 | 3.080   | 4.540   | 0.0246 |               |
| 17 | 5.780 | 3.550   | 4.785   | 0.0270 |               |
| 18 | 7.275 | 4.410   | 4.525   | 0.0204 | 0.0487        |
| 19 | 4.570 | 3.465   | 4.625   | 0.0264 |               |
| 20 | 7.845 | 3.400   | 4.480   | 0.0252 | 0.0386        |
| 21 | 5.450 | 3.465   | 3.995   | 0.0228 |               |
| 22 | 5.370 | 3.130   | 4.515   | 0.0282 | 0.0233        |
| 23 | 5.055 | 3.745   | 4.065   | 0.0300 |               |
| 24 | 6.000 | 3.715   | 4.555   | 0.0276 |               |
| 25 | 7.070 | 4.230   | 4.555   | 0.0222 |               |
| 26 | 6.895 | 4.005   | 4.585   | 0.0216 |               |
| 27 | 7.085 | 3.200   | 4.435   | 0.0216 | 0.0313        |
| 28 | 5.370 | 3.480   | 4.315   | 0.0240 |               |
| 29 | 5.665 | 3.045   | 4.520   | 0.0294 |               |
| 30 | 4.085 | 3.240   | 4.530   | 0.0300 | 0.0355        |
| 31 | 4.585 | 3.470   | 4.350   | 0.0288 |               |
| 32 | 3.650 | 3.460   | 4.620   | 0.0150 | 0.0911        |
| 33 | 3.985 | 2.875   | 4.320   | 0.0294 |               |
| 34 | 4.265 | 3.435   | 4.710   | 0.0210 | 0.0355        |
| 35 | 3.815 | 3.260   | 4.655   | 0.0258 | 0.0956        |
| 36 | 7.730 | 3.310   | 4.410   | 0.0252 | 0.0283        |
| 37 | 4.650 | 3.425   | 4.560   | 0.0258 |               |

Portions of 12 of the original samples were enforced with urea (that is, urea was added thereto), and the absorption spectra of those, as well as the 37 original samples were obtained using a Perkin-Elmer 1710 Fourier Transform Infra-Red (FTIR) spectrophotometer controlled by an IBM-PC-compatible computer running a Perkin-Elmer IR-DataManager software. The measuring compartment of the instrument contained two identical interchangeable cuvettes (sample shuttle) with calcium fluoride ($CaF_2$) windows and a sample path of 37 μm. Each cuvette was thermostated to 40° C.

Calibration according to the invention

The 49 samples were homogenized, injected into the sample cuvette, and an IR spectrum in the range 4000-900 cm$^{-1}$ was recorded. Distilled water was used as reference, and the resolution was selected to be 2 cm$^{-1}$ giving a total of 3101 data points. The spectra were collected in digitized form and stored on a disk for later numerical analysis.

Prior to statistical analysis the 50 spectra (49 samples and distilled water) were reduced to 1165 data points, firstly by removing the data points in the regions of water absorptions (3700 cm$^{-1}$ (2.70 μm) to 3000 cm$^{-1}$ (3.33 μm) and 1689 cm$^{-1}$ (5.92 μm) to 1610 cm$^{-1}$ (6.21 μm)), and secondly by reducing the number of data points in those regions of the spectrum containing little spectral information 4000 cm$^{-1}$ (2.50 μm) to 3700 cm$^{-1}$ (2.70 μm) and 2759 cm$^{-1}$ (3.62 μm) to 1809 cm$^{-1}$ (5.53 μm).

The 49 samples were subjected to Partial Least Squares analysis (as described, e.g. in "Multivariate Calibration" by Harald Martens and Tormod Naes, John Wiley & Sons, London, 1989, pp 116-125), thereby calibrating the system resulting in a set of regression equations characteristic to the calibrated system.

Results

The regression equation for urea consists of a set of terms comprising a regression coefficient (B-coefficient) as found by Partial Least Squares regression, and the corresponding absorbance value at each of the 1165 spectral points. In FIG. 1 the regression coefficients found, using 7 calibration factors on mean centered data, are shown together with an absorption spectrum of pure urea in water (approximately 5% solution) in the spectral region from 1600 cm$^{-1}$ (6.25 μm) to 1000 cm$^{-1}$ (10.0 μm).

The strongest absorption of urea is found between 1700 and 1650 cm$^{-1}$, but this spectral region can not be used under the experimental conditions used, due to strong absorption of water in the same region. FIG. 1 shows that the regression coefficients found by the PLS calibration, show characteristics which closely resembles the spectral characteristics of urea dissolved in water. Other features in the regression spectrum can be contributed to the major components of milk, fat, protein and lactose.

FIG. 2 shows the absorbance spectrum of sample 15 (0.0168% urea) as well as the spectrum recorded of the same sample after enforcement by pure urea (0.0552% urea). The difference between the two spectra at the urea absorption between 1500 cm$^{-1}$ (6.67 μm) and 1450 cm$^{-1}$ (6.90 μm), shown in FIG. 3, amounts to about 0.05 absorbance units, approximately twice the measurement noise in the same region.

Conclusion

The above results demonstrate that it is possible to perform calibration for urea in concentrations less than 0.01%, in milk in the presence of the compounds with spectral features which interfere with urea, showing concentration variation 100-500 times the variation of urea, fat (3.3-7.3%), protein (2.9-4.5%) and lactose (4.0-4.8%).

EXAMPLE 2

Measurement of urea in an infrared attenuation measuring system using natural milk samples, measured using discrete filters.

The sample material used in this experiment, was 380 natural milk samples from individual cows.

One portion of each sample was analyzed for urea in a segmented flow analyzer, using a method comprising enzymatic decomposition of urea to ammonium and carbonate, followed by spectrophotometric determination of ammonium as an indirect measure of urea.

The IR absorption of each sample was also measured, using a MilkoScan 605 IR instrument manufactured by Foss Electric, Hillerød, Denmark, in nine different wavebands, after homogenising with the built-in homogenizer of the MilkoScan. The instrument was equipped with 9 filters, allowing measurements of the IR absorption at the following wavenumbers: 2817 cm$^{-1}$ (3.55 μm), 2853 cm$^{-1}$ (3.50 μm), 1739 cm$^{-1}$ (5.75 μm), 1493 cm$^{-1}$ (6.70 μm), 1538 cm$^{-1}$ (6.50 μm), 1393 cm$^{-1}$ (7.70 μm), 1053 cm$^{-1}$ (9.50 μm), 1388 cm$^{-1}$ (7.20 μm) and 1464 cm$^{-1}$ (6.83 μm), all filters having spectral bandwith of approximately 20 cm$^{-1}$ (full width at 50% intensity FWHM).

The 380 natural milk samples were subjected to Partial Least Squares analysis (as described, e.g. in "Multivariate Calibration" by Harald Martens and Tormod Naes, John Wiley & Sons, London, 1989, pp 116-125), thereby calibrating the system resulting in a set of regression equations characteristic to the calibrated system using all available samples for calibration.

The absorbance values of the sample set was subject to factor analysis, in order to identify a subset of the samples which represented the spectral variation of the 380 samples in a such a way as to allow satisfactory calibration. As a result of the factor analysis 16 samples were chosen as a calibration set.

The calibration set was subjected to Partial Least Squares analysis, thereby calibrating the system resulting in a set of regression equations characteristic to the calibrated system.

Results

The regression equation for urea, consisting of a set of terms comprising a regression coefficient (B-coefficient) as found by Partial Least Squares regression applied to the calibration set, and the corresponding absorbance value at each of the 9 filters, was used to predict the concentration of urea in each of the natural milk samples for both calibrations. The resulting prediction of urea using, firstly all 380 samples, and secondly using the 16 samples selected using factor analysis for the calibration, is shown in FIG. 4 and 5 respectively, which show a plot of measured urea concentration versus predicted urea concentration.

The Standard Error of Prediction (SEP) obtained using either all the 380 samples, or the 16 samples selected using factor analysis, was found to be 0.0037 and 0.0040% urea respectively. The repeatability error, defined as the difference in predicted urea concentration when the same samples were measured more than once, was in both calibration models found to be 0.0017% urea.

We claim:

1. A method for determining, with an accuracy better than 0.007%, expressed as Standard Error of Prediction, the concentration of urea in a concentration range of 0–0.1% in a milk sample containing at least 1% fat, at least 1% dissolved lactose, and at least 1% protein, by an infrared absorption measuring technique, said method comprising the steps of:
  (a) determining absorption in an infrared radiation waveband from 1000 cm$^{-1}$ (10.0 μm) to 4000 cm$^{-1}$ (2.50 μm) of the milk sample, wherein at least one determination is made in a waveband from 1000 cm$^{-1}$ (10.0 μm) to 1800 cm$^{-1}$ (5.56 μm) in which urea absorbs, wherein at least one determination is made in a waveband in which fat absorbs, wherein at least one determination is made in a waveband where lactose absorbs, and at least one determination is made in a waveband where protein absorbs;
  (b) determining, on the basis of said absorption determinations and predetermined parameters established by multivariate calibration, a contribution from fat, lactose, and protein in said waveband where urea absorbs, and
  (c) quantitatively assessing the concentration of urea in the milk sample on the basis of the absorption in the waveband where urea absorbs and on the basis of the determined contribution from fat, lactose, and protein in said waveband.

2. A method according to claim 1, wherein the predetermined parameters established by multivariate calibration are obtained using milk samples containing known concentrations of urea, or milk samples to which known concentrations of urea have been added.

3. A method according to claim 1, wherein more than one determination is made in the wavebands where urea, fat, lactose, and protein absorb.

4. A method according to claim 1, wherein concentrations of the components fat, lactose, and protein are predicted and each prediction is based on at least one measurement in a waveband in which the component absorbs.

5. A method according to claim 1, wherein the multivariate calibration is performed using milk samples containing known concentrations of urea, fat, lactose and/or protein, and/or milk samples to which known concentrations of urea, fat, lactose and/or protein have been added.

6. A method according to claim 5, wherein the physical conditions (temperature, degree of homogenization) of the milk samples used to perform the multivariate calibration have been modified.

7. A method according to claim 1, wherein the multivariate calibration has been performed using at least 4 milk samples.

8. A method according to claim 7, wherein the multivariate calibration has been performed using at least 8 milk samples.

9. A method according to claim 8, wherein the multivariate calibration has been performed using at least 12 milk samples.

10. A method according to claim 9, wherein the multivariate calibration has been performed using at least 18 milk samples.

11. A method according to claim 10, wherein the multivariate calibration has been performed using at least 25 milk samples.

12. A method according to claim 1, wherein the Standard Error of Prediction (SEP) is better than 0.005%.

13. A method according to claim 12, wherein the Standard Error of Prediction (SEP) is better than 0.004%.

14. A method according to claim 1, wherein the at least one determination in which urea absorbs is made in the waveband from 1100 cm$^{-1}$ (9.09 μm) to 1800 cm$^{-1}$ (5.56 μm).

15. A method according to claim 14, wherein the at least one determination in which urea absorbs is made in the waveband from 1400 cm$^{-1}$ (7.14 μm) to 1500 cm$^{-1}$ (6.67 μm).

16. A method according to claim 14, wherein the at least one determination in which urea absorbs is made in the waveband from 1500 cm$^{-1}$ (6.67 μm) to 1800 cm$^{-1}$ (5.56 μm).

17. A method according to claim 14, wherein the at least one determination in which urea absorbs is made in the waveband from 1100 cm$^{-1}$ (9.09 μm) to 1200 cm$^{-1}$ (8.33 μm).

18. A method according to claim 1, wherein the absorption determinations are performed in wavebands defined by optical filters.

19. A method according to claim 1, wherein the absorption determinations are performed in wavebands defined by stationary grating and movable and/or multiple detectors or by a movable grating and one or several stationary or movable detectors.

20. A method according to claim 1, wherein the absorption determinations are performed using a Fourier transform interferometer.

21. A method according to claim 1, wherein the absorption determinations are performed using an ATR technique.

22. A method according to claim 1, wherein the absorption determinations are made using a transmission technique.

23. A method according to claim 22, wherein the infrared light is transmitted through a cuvette containing the milksample, a path length of the cuvette being at most 200 μm.

24. A method according to claim 23, wherein the infrared light is transmitted through a cuvette containing the milk sample, the pathlength of the cuvette being at most 50 μm.

25. A method according to claim 1, wherein the multivariate calibration is performed by a method selected from the group consisting of Partial Least Squares algorithm, Principal Component Regression, Multiple Linear Regression, and Artificial Neural Network learning.

26. A method according to claim 1, wherein any fat globules in the milk sample have a mean diameter of at most 3 μm.

27. A method according to claim 1, wherein compensation for influence on the urea measurement is further performed for one or several of the following components: citric acid, free fatty acids, antibiotics, phosphates, somatic cells, bacteria, preservatives and casein, by performing, for each component, a determination of infrared absorption in a waveband in which the component absorbs, the compensation being performed on the basis of multivariate calibration by combining the results, for all components for which compensation is to be made, from the determinations made in the wavebands where the components absorb.

* * * * *